United States Patent
Jensen et al.

(10) Patent No.: US 7,638,073 B2
(45) Date of Patent: Dec. 29, 2009

(54) PHOTOCHROMIC MATERIAL COMPRISING A PROTEORHODOPSIN APOPROTEIN AND A RETINAL ANALOG

(75) Inventors: Rasmus B. Jensen, Hedehusene (DK); Bradley R. Kelemen, Menlo Park, CA (US); Donald E. Ward, II, Los Altos, CA (US); Alfred E. Asato, Waipahu, HI (US)

(73) Assignee: Genencor International, Inc., Palo Alto, CA (US)

( * ) Notice: Subject to any disclaimer, the term of this patent is extended or adjusted under 35 U.S.C. 154(b) by 31 days.

(21) Appl. No.: 11/569,864

(22) PCT Filed: Jun. 9, 2005

(86) PCT No.: PCT/US2005/020900

§ 371 (c)(1),
(2), (4) Date: Dec. 13, 2007

(87) PCT Pub. No.: WO2005/124230

PCT Pub. Date: Dec. 29, 2005

(65) Prior Publication Data

US 2008/0290328 A1 Nov. 27, 2008

Related U.S. Application Data

(60) Provisional application No. 60/579,180, filed on Jun. 10, 2004, provisional application No. 60/622,425, filed on Oct. 26, 2004.

(51) Int. Cl.
*C07C 231/00* (2006.01)
*C12Q 1/68* (2006.01)
(52) U.S. Cl. .......... 252/500; 554/35; 554/221; 568/420; 568/446; 568/445; 435/6; 435/69.1; 435/252.3

(58) Field of Classification Search ............ 252/500; 250/226; 554/35
See application file for complete search history.

(56) References Cited

U.S. PATENT DOCUMENTS 4,896,049 A * 1/1990 Ogawa ............... 250/226

(Continued)

OTHER PUBLICATIONS

Muthyala et a/., "Alkylated Azulenic Retnal and Bacteriorhodopsin Analogs," Tetrahedron Letters, vol. 19, pp. 5-8 (1998).*

(Continued)

*Primary Examiner*—Harold Pyon
*Assistant Examiner*—Timothy Chiang
(74) *Attorney, Agent, or Firm*—Howrey LLP; Viola T. Kung (57) ABSTRACT

The present invention relates to a photochromic material comprising a proteorhodopsin apoprotein and a retinal analog. In one embodiment, the retinal analog is an azulenic retinoid compound. In another embodiment, the retinal analog is a compound that is structurally similarly to all-trans-retinal. The proteorhodopsin apoprotein and the retinal analog form a photochromic material having different spectral properties from those of a corresponding photochromic material formed by the same proteorhodopsin apoprotein and all-trans-retinal. In one embodiment of the application, the retinal analog-containing proteorhodopsin has an absorbance spectrum that does not overlap significantly with that of all-trans-retinal-containing proteorhodopsin. In another embodiment of the application, the retinal analog-containing proteorhodopsin yields a red-shifted visual chromophore compared with the all-trans-retinal-containing proteorhodopsin chromophore. The photochromic material of the present invention is useful as an optical data storage carrier, a fraud-proof optical data carrier, security ink, and in other optical applications.

15 Claims, 4 Drawing Sheets

U.S. PATENT DOCUMENTS 5,235,076 A * 8/1993 Asato et al. .................. 554/35
2003/0104375 A1 * 6/2003 Delong et al. ................. 435/6

OTHER PUBLICATIONS

Bell et al., Photoactivities of the Red-Shifted Azulenic Bacteriorhodopsin Analogues, Journal of Physical Chemistry A, vol. 102, pp. 5481-5483 (1998.).*

Rudiger et al., "Reconstitution of Bacteriorhodopsin from the Apoprotein and Retinal Studied by Fourier-Transform Infrared Spectroscopy," *Biochemistry*, vol. 36, pp. 4867-4874 (1997).

Khodonov et al., "Modified Bacteriorhodopsins as a Basis for New Optical Devices," *Sensors and Actuators B*, vol. 38-39, pp. 218-221 (1997).

Bell et al., Photoactivities of the Red-Shifted Azulenic Bacteriorhodopsin Analogues, *Journal of Physical Chemistry A*, vol. 102, pp. 5481-5483 (1998).

Muthyala et al., "Alkylated Azulenic Retnal and Bacteriorhodopsin Analogs," *Tetrahedron Letters*, vol. 19, pp. 5-8 (1998).

Imai et al., "Probing for the Threshold Energy for Visual Transduction: Red-Shifted Visual Pigment Analogs from 3-Methoxyl-3-Dehydroretinal and Related Compounds," *Photochemistry and Photobiology*, vol. 70, No. 1, pp. 111-115 (1999).

Beja et al., "Bacterial Rhodopsin: Evidence for a New Type pf Phototrophy in the Sea," *Science*, vol. 289, pp. 1902-1906 (2000).

Beja et al., "Protohodopsin phototrophy in the ocean," *Nature*, vol. 411, pp. 786-789 (2001).

Dioumaev et al., "Proton Transport by Proteorhodopsin Requires that the Retinal Schiff Base Counterion Asp-97 Be Anionic," Biochemistry, vol. 42, pp. 6582-6587 (2003).

Man et al., "Diversification and Spectral Tuning In Marine Protoeorhodopsins," *The EMBO Journal*, vol. 22, No. 8, pp. 1725-1731 (2003).

Sabehi, et al., "Novel Proteorhodopsin Variants from the Mediterranean and Red Seas," *Environmental Microbiology*, vol. 5, pp. 842-849 (2003).

Venter et al., "Environmental Genome Shotgun Sequencing of the Sargasso Sea," *Science*, vol. 304, pp. 66-74 (2004).

Dioumaev et al., "Proton Transfers in the Photochemical Reaction Cycle of Proteorhodopsin," Biochemistry, vol. 41, pp. 5348-5358 (2002).

Int'l Search Report, PCT/US05/20900, mailed Nov. 1, 2005.

* cited by examiner

PHOTOCHROMIC MATERIAL COMPRISING A PROTEORHODOPSIN APOPROTEIN AND A RETINAL ANALOG

This application is a National Stage of International Application PCT/US2005/020900, filed Jun. 9, 2005, published Dec. 29, 2005, under PCT Article 21(2) in English; which claims the priority of U.S. Provisional Applications 60/579,180, filed Jun. 10, 2004, and 60/622,425, filed Oct. 26, 2004.

FIELD OF INVENTION

The present invention relates to a photochromic material comprising a proteorhodopsin apoprotein and a retinal analog such as azulenic retinoid compounds and other compounds. The proteorhodopsin apoprotein and the retinal analog form a photochromic material having different spectral properties from those of a photochromic material formed by the same proteorhodopsin apoprotein and all-trans-retinal. The photochromic material of the present invention can be used in an optical data storage carrier, a fraud-proof optical data carrier, security ink, and in other optical applications.

BACKGROUND OF THE INVENTION

Bacteriorhodopsin (BR) is a retinal protein molecule found in the photosynthetic system of a salt-marsh bacterium called *Halobacterium salinarium*. The BR molecules are located in the cell membrane, forming a 2D protein-lipid array, commonly called the purple membrane. The use of photochromic proteins like bacteriorhodopsin (BR) for optical data storage has been considered promising. BR-based optical films have been worked on for the past two decades, but these films do not have the required properties to make them commercially viable for data storage applications. One of the problems with the BR-based films is that BR forms 0.2-1 µm sized protein-lipid patches. If BR is extracted from these patches to form a monomeric protein, it becomes unstable and is inactivated in a few days. The problem with using these BR patches in optical films is that the patches are approximately the same size as the wavelength of the light used to interface with the film, which results in significant light scattering during read and write cycles, thereby increasing noise and degrading the performance of the film. Additionally, the BR patches tend to stick to each other, which result in uneven distribution of the BR protein in the film, and further degrade the performance of BR-based optical films.

Another problem of BR is that it is expensive to produce in large quantity. BR has to be expressed in its natural organism *H. salinarum* for it to be fully functional. Dunn, et al., *J Biol Chem*, 262: 9246-9254 (1987); Hohenfeld, et al., *FEDB lett*, 442: 198-202 (1999)). *H. salinarum* grows very slowly, gives a low cell density and requires the presence of large amounts of salt in the growth medium. The low productivity of *H. salinarum* and the need for expensive custom-made fermentation and recovery equipment that can tolerate the high salt growth medium result in high cost of BR production.

Proteorhodopsins (PRs) are distantly related to bacteriorhodopsin (22-24% sequence identity). Proteorhodopsins are integral membrane proteins; they are isolated from uncultivated marine eubacteria and function as light-driven proton pumps. Upon absorption of light by the all-trans-retinal cofactor, proteorhodopsin goes through a photocycle with a number of intermediates. It is believed that upon excitation of the proteorhodopsin molecule by light stimulation, a proteorhodopsin/retinal complex is excited to an unstable intermediate energy state. Proteorhodopsin progresses through a series of unstable energy states that can vary in terms of energy plateaus or intermediates, e.g., an "M-like state" or "M-state", a "K-like state" or "K-state", an "N-like state" or "N-state", or an "O-like state" or "O-state". Subsequently, the complex reverts to a more stable basal state concomitant with transport of a proton.

Proteorhodopsin and bacteriorhodopsin are different families of proteins. These proteins have some shared characteristics, but also have clearly different properties. Proteorhodopsins are more advantageous to use in some technical applications than bacteriorhodopsins because of the ease of expressing and producing proteorhodopsins. Proteorhodopsin can be functionally expressed in *E. coli*, a bacterial host capable of rapid high-level protein expression. Thus, production of proteorhodopsin is more economic and efficient than production of bacteriorhodopsin.

Béjà, et al. (*Science* 289:1902-6, 2000) disclose the cloning of a proteorhodopsin gene from an uncultivated member of the marine γ-proteobacteria (i.e., the "SAR86" group). The proteorhodopsin was functionally expressed in *E. coli* and bound all-trans-retinal to form an active light-driven proton pump.

Béjà, et al. (*Nature* 411:786-9, 2001) disclose the cloning of over twenty variant proteorhodopsin genes from various sources. The proteorhodopsin variants appear to belong to an extensive family of globally distributed proteorhodopsin variants that maximally absorb light at different wavelengths.

Dioumaev, et al. (Biochemistry, 42: 6582-6587 (2003)) disclose using proteorhodopsin-containing membrane fragments encased in polyacrylamide gel for flash photolysis and measurements of absorption changes in the visible range.

U.S. Pat. No. 5,235,076 (Asato) discloses azulenic retinoid compounds and therapeutic compositions. The compositions are useful in treating dermatological disorders such as acne and psoriasis.

U.S. Pat. No. 4,896,049 (Ogawa) discloses various synthetic analogs of retinal, which have different absorption wavelengths. The synthetic retinal analogs disclosed in Ogawa are incorporated herein by reference.

Khodonov, et al. (*Sensors and Actuators B* 38-39:218-221 (1997)) describe modified bacteriorhodopsin by replacing the natural bacteriorhodopsin chromophore, all-trans-retinal, with its analogs. The retinal analogs disclosed in Khodonov are incorporated herein by reference.

Imai, et al. (*Photochemistry and Photobiology*, 70: 111-115 (1999)) disclose that azulenic retinal analogs failed to yield a red-shifted visual pigment analog, whereas the 9-cis isomers of the polyenals 3-methoxy-3-dehydroretinal and 14F-3-methoxy-3-dehydroretinal yielded iodopsin pigment analogs at 663 and 720 mm.

Optical data storage has the potential to revolutionize the computer industry, since optical data storage provides a very high storage capacity and rapid reading and writing of data. Additionally, optical signal processing could be used in a highly parallel fashion for pattern recognition, which is difficult to do with the current computing technologies. A functional optical material with low light scattering is required for these applications to succeed.

Documents like banknotes, checks, identity cards etc. often incorporate security features to make them difficult to copy or counterfeit. Most of these are based on either using special paper with security features like watermarks incorporated during paper manufacturing, or printing hairline patterns that are difficult to copy. However, such features are permanently visible and do not meet sophisticated security requirements.

There are needs for optical information carriers that can be produced efficiently and economically and have low background noise. Such optical information carriers are effective as optical data storage material or fraud-proof optical data carriers. Proteorhodopsins having different chromophores provides an improvement of optical information carriers.

The most red-shifted natural visual pigment ($\lambda_{max}$=630 mm) is identified in fish retinas, which has 3-dehydroretinal as its chromophore (Imai, supra). There is a need for red-shifted proteorhodopsin/retinal analog compositions such that cost-effective red laser can be used in the optical storage device reader.

SUMMARY OF THE INVENTION

The present invention is directed to a photochromic material useful for optical applications. The photochromic material comprises a proteorhodopsin apoprotein and a retinal analog. In one embodiment, the retinal analog is an azulenic retinoid compound. In another embodiment, the retinal analog is a compound that is structurally similarly to all-trans-retinal.

The proteorhodopsin apoprotein and the retinal analog form a photochromic material having spectral properties significantly different from those of a corresponding photochromic material formed by the same proteorhodopsin apoprotein and all-trans-retinal. In one embodiment of the application, a proteorhodopsin apoprotein and a retinal analog form a photochromic material having an absorbance spectrum that does not overlap significantly with that of all-trans-retinal-containing proteorhodopsin. In another embodiment of the application, a proteorhodopsin apoprotein and a retinal analog form a photochromic material that yields a red-shifted visual chromophore compared with the all-trans-retinal chromophore.

The photochromic material of the present invention can be used in an optical data storage carrier, a fraud-proof optical data carrier, security ink, and in other optical applications.

DETAILED DESCRIPTION OF THE INVENTION

Definitions

As used herein, the term "actinic light" refers to radiant energy, especially in the visible and ultraviolet spectral regions, which can produce photochromic changes in a photochromic material.

As used herein, the term "apoprotein" refers to the protein part of a conjugated protein. A "proteorhodopsin or bacteriorhodopsin apoprotein" refers to the proteorhodopsin or bacteriorhodopsin protein itself without the all-trans-retinal or retinal analog.

As used herein, the term "azulenic retinoid compound" refers to a compound having azulenic group attached to a modified or non-modified all-trans-retinal backbone.

As used herein, the term "basal state" or "B-state" or "B-like state" refers to the basal state of the photocycle of a proteorhodopsin molecule or a bacteriorhodopsin molecule without light excitation. The term "M-state" or "M-like state" refers to an excited spectral state in a photocycle as compared with the basal state.

As used herein, "photochromic" refers to having the capability to change color upon exposure to radiant energy (as light).

As used herein, the term "retinal analog" refers to a compound that replaces all-trans retinal and is capable of coupling with the apoprotein of a proteorhodopsin.

The inventors have discovered that certain retinal analogs can be incorporated into proteorhodopsin apoproteins, produce a photocycle, and form useful photochromic materials.

The present invention is directed to a photochromic material comprising a proteorhodopsin apoprotein and a retinal analog. In one embodiment, the retinal analog is an azulenic retinoid compound. In another embodiment, the retinal analog is a compound that is structurally similarly to all-trans-retinal.

The proteorhodopsin apoprotein and the retinal analog form a photochromic material having spectral properties different from those of a corresponding photochromic material that is formed by the same proteorhodopsin apoprotein and all-trans-retinal. The differences in spectral properties provide the opportunity to use multiple wavelengths of light to increase capacity of optical data storage and/or allow parallel processing. The differences in spectral properties further provide different colors of proteorhodopsins in security ink applications. The red-shifted retinal analog-containing proteorhodopsins can be used with a red laser, which is cost effective compared with a green laser needed for all-trans retinal containing proteorhodopsins.

Proteorhodopsin is a trans-membrane protein with a structure of seven lipid membrane-spanning α-helices that form a generally cylinder shaped channel. When folded correctly and supplied with all-trans-retinal, the seven α-helices of proteorhodpsin are arranged as a cage surrounding the all-trans-retinal. Proteorhodopsin apoprotein binds all-trans-retinal at a conserved lysine residue (K231 in Bac31A8 and K234 in Hot75M1) by a Schiff-base linkage to form a pigment that absorbs in the visible wavelength range of light. A naturally occurring proteorhodopsin apoprotein and all-trans-retinal in general form a photochromic material having a maximum absorbance wavelength ranges from about 480-550 nm, often between 488-526 nm. (Man, et al. Embo J. 22:1725-1731 (2003))

In one embodiment of the application, a proteorhodopsin apoprotein binds to a retinal analog and form a photochromic material, whose absorbance spectrum does not overlap significantly from the absorbance spectrum of a corresponding photochromic material formed by the same proteorhodopsin apoprotein and all-trans-retinal. By "not overlap significantly," it is meant that a particular wavelength can be selected such that the absorbance (optical density) at that wavelength of one proteorhodopsin is at least 2, at least 3, at least 4, at least 5, at least 6, at least 7, at least 8, at least 9, or at least 10 times higher than the absorbance of another proteorhodopsin under the same conditions (e.g. temperature). For example, at 600 nm, if photochromic material X has an absorbance of 1.0 OD, and photochromic material Y has an absorbance equal to or less than 0.5, preferably 0.33, preferably 0.2, more preferably 0.1 OD, then the absorbance spectra of photochromic materials X and Y do not overlap significantly. By providing different absorption spectra, the photochromic materials of the present invention provide multi-colors and/or increase capacity of the optical data storage.

In another embodiment of the application, a proteorhodopsin apoprotein binds to a retinal analog and form a photochromic material that yields a red-shifted chromophore compared with the corresponding complex formed by the same proteorhodopsin apoprotein and all-trans-retinal. The maximum absorbance wavelength of the photochromic material of the present invention ranges from 550-750 nm, preferably 600-700 nm, more preferably 625-650 nm, which is red-shifted from that of the complex formed by the same proteorhodopsin apoprotein and all-trans-retinal. The red-shifted chromophores are useful, for example, to be used with red laser as the writing (actinic) light source.

All-Trans-Retinal

The structure of all-trans-retinal is shown as following:

Retinal Analogs

The retinal analogs include azulenic retinoid compounds of Formula I:

Formula I wherein R', R" and R'" are each independently H, $C_{1-4}$ straight chain alkyl, or $C_{1-4}$ branched chain alkyl, n is an integer from 1 to 4;

$X_a$ and $X'_b$ are each independently H, $C_{1-4}$ alkyl, F, Cl or $CF_3$;

Y is absent, or Y is a para-, meta-, or ortho-phenyl; and

Z is CHO.

In one embodiment of the invention, R', R" and R'" are independently H, methyl, isopropyl. Preferably, R'=R'"=methyl, R"=isopropyl.

In a preferred embodiment of the invention, Y is absent.

The preparation of azulenic retinoid compounds is disclosed, for example, in U.S. Pat. No. 5,235,076 (Asato), which is incorporated herein by reference in its entirety.

Specific examples of Formula I that are useful for the present invention include the following compounds:

-continued

Compound I

Compound J

Compound K

Compound L

Compound M

Compound N

The retinal analogs useful for the present invention also include the following non-azulenic compounds that are structurally similar to all-trans-retinal:

Compound O

(U.S. Pat. No. 4,896,049 (Ogawa))

Compound P

(U.S. Pat. No. 4,896,049 (Ogawa))

Compound Q (U.S. Pat. No. 4,896,049 (Ogawa))

Compound R

Khodonov, et al. (*Sensors and Actuators B* 38-39:218-221 (1997))

Compound S

Khodonov, et al. (*Sensors and Actuators B* 38-39:218-221 (1997))

P-dimethyl aminocinnamaldehyde (DMCA)

DMCA is commercially available, for example, from Fluka AG (Buchs, Switzerland) through Sigma-Aldrich (St. Louis, Mo.), The Lab Depot, Inc. (Alpharetta, Ga.) and the Science Lab.com (Kingwood, Tex.).

Proteorhodopsins

Proteorhodopsins useful for the present invention can be derived from any naturally occurring proteorhodopsin. Various natural nucleic acid sequences, encoding various natural proteorhodopsins, have been obtained from naturally occurring members of the domain bacteria. Such members include marine bacteria, such as bacteria from the SAR86 group. The natural nucleic acid sequences of proteorhodopsins are cloned and the natural form of proteorhodopsins is expressed. There are many natural forms of proteorhodopsins; including those derived from marine bacteria and those derived from non-marine bacteria; all of which can be used for the present invention.

For example, natural forms of proteorhodopsins include Hot75 ml, Bac31A8, Bac40E8, Bac41B4, Bac64A5, Hot0m1, Hot75m3, Hot75m4, Hot75m8, MB0m1, MB0m2, MB20m2, MB20m5, MB20m12, MB40m1, MB40m5, MB100m5, MB100m7, MB100m9, MB100m10, PalB1, PalB2, PalB5, PalB7, PalB6, PalB8, PalE1, PalE6, PalE7, MED26, MED27, MED36, MED101, MED102, MED106, MED25, MED202, MED204 MED208, REDA9, REDB9, REDF9, RED19, RED2, RED23, RED27, RED30, RED4, RED5, REDr6a5a14, REDr6a5a6, REDr7_1_4, REDs3_7, REDr7_1_15, REDs3_15, medA15r8ex6, REDr7_1_16, medA5r11b9, medA15r9b5, medA15r8b3, medA15r11b3, medA15_r8_1, medA17R9_1, medA15r8b9, medA19_R8_16, medA19_R8_19, medA17_R8_6, mredA15r9b7, medA15_R8_3, medA15r10b5, medA19_r9_9, medA15_r8ex7, medA19_R8_20, medA15_R8ex9, medA15_r9_3, medA17_r8_15, medA17_r8_11, medA15r8b8, medA15r8ex4, ANT32C12 PR and HOT2C01 PR. See Baja, et al., Nature 411:786-9 (2001); Man, et al., EMBO J., 22:1725-1731 (2003); and Sabehi, et al., Environ. Microbiol., 5: 842-9 (2003). The nucleotide and amino acid sequences of the above various proteorhodopsins have been deposited with Genbank under accession numbers AF349976-AF350003, AF279106, AY210898-AY210919, AY250714-AY250741, AY372453 and AY372455. In addition, Venter, et al. (Science 304: 66-74 (2004)) recently have reported 782 new rhodopsin analogs, most of which are proteorhodopsins, found in the Sargasso Sea. The proteorhodopsins described in the above references are suitable for the present invention.

Proteorhodopsins useful for the present invention can also be derived from any non-naturally occurring proteorhodopsins, such as proteorhodopsin mutants. The term "proteorhodopsin mutant" refers to a proteorhodopsin comprising one or more mutations that insert, delete, and/or substitute one or more amino acid residues and/or nucleotides from the natural sequences of proteorhodopsins. For example, the nucleotide sequence can be altered by a substitution of a different codon that encodes the same or a functionally equivalent amino acid residue within the sequence, thus producing a silent change. For example, an amino acid residue within the sequence can be substituted by another amino acid of a similar polarity, or a similar class. Non-polar (hydrophobic) amino acids include alanine, leucine, isoleucine, valine, proline, phenylalanine, tryptophan, glycine and methionine. Polar neutral amino acids include serine, threonine, cysteine, tyrosine, asparagine, and glutamine. Positively charged (basic) amino acids include arginine, lysine, and histidine. Negatively charged (acidic) amino acids include aspartic and glutamic acid.

Proteorhodopsin mutants useful for the present invention, for example, include the amino acid sequence of Bac31A8H75K, Bac31A8H75N, Bac31A8H75Q, Bac31A8 E108Q, Bac31 A8 D97N, Hot75 ml H77K, Hot75 ml H77N, Hot75 ml H77Q, Hot75 ml H77E, Hot75 ml H77D, Hot75 ml H77W, Hot75 ml R96A, Hot 75 ml E 110Q, Hot75 ml D99N, Hot75 ml R96B, and Hot75 ml R96Q. In which, Bac31A8H75K means that the 75 amino residue of the naturally occurring Bac31A8 is mutated from histidine to lysine. Proteorhodopsin mutants have been disclosed in the co-pending U.S. Application Publication No. 2005-0095605; which is incorporated herein by reference in its entirety.

The retinal analog-containing proteorhodopsin can be conveniently prepared by expressing proteorhodopsin in the presence of a retinal analog in a host cell. E. coli, for example, is an effective host cell because it does not produce all-trans-retinal. Other host cells, in which the synthetic pathway of all-trans-retinal is blocked, can also be effective host cells for preparing the analog-containing proteorhodopsins. The analog is added to the cell culture and inserted into the proteorhodopsin protein during host cell growth and proteorhodopsin expression. The retinal analog-containing bacteriorhodopsin, on the other hand, cannot be prepared conveniently by adding the analog during the expression of bacteriorhodopsin in its host cell H. salinarum. All-trans-retinal is produced by H. salinarum, and the all-trans-retinal-containing bacteriorhodopsin is formed during the expression of bacteriorhodopsin. In order to prepare retinal analog-containing bacteriorhodopsin, all-trans-retinal has to be removed from the retinal-containing bacteriorhodopsin, then the retinal analog added to the bacteriorhodopsin apoprotein to form a complex of bacteriorhodopsin and the retinal analog.

Immobilized Retinal Analog-Containing Proteorhodopsin

The present invention provides a solid material comprising an immobilized retinal analog-containing proteorhodopsin. The solid material comprises one or more hydrophilic polymers that are capable of forming a homogeneous phase with the retinal analog-containing proteorhodopsin prior to solidification to a solid form, such that the retinal analog-containing proteorhodopsin is evenly distributed in the solid. By "homogeneous" is meant that the retinal analog-containing proteorhodopsin and the hydrophilic polymer or its precursor form a uniform structure or composition throughout the mixture. By "immobilized" as used herein, is meant that proteorhodopsin is not mobile, and is fixed within the material. The interaction between proteorhodopsin and the material can be covalent or non-covalent. For example, proteorhodopsin can be physically entrapped within the material. Proteorhodopsin can also bind to the material by electrostatic charges, H-bond, hydrophobic, hydrophilic, or van der Waals interaction. By immobilization, the proteorhodopsin molecules are fixed and do not diffuse or diffuse very slowly within the solid material, such that an optical signal is not lost by diffusion of the proteorhodopsin molecules.

The hydrophilic polymers produce a non-opaque or optically transparent solid material, which allows efficient light excitation of photochromic material contained thereof.

Hydrophilic polymers suitable for this invention include silica sol gel, gelatin, polyacrylamide, acacia, agar, calcium carrageenan, calcium alginate, sodium alginate or other salts of alginic acid, algin, agarose, collagen, methyl cellulose, polyethylene glycol, sodium carboxy methyl cellulose, polyacrylic acid, partially cross-linked polyacrylic acid, hydroxyethyl cellulose, hydroxypropyl cellulose, hydroxypropylmethyl cellulose, polyethylene oxide, pectin and mixtures thereof.

Vinyl polymers and derivatives thereof are also useful in the present invention. Polyvinyl alcohol (PVA), is defined as a homopolymer or copolymer, in which vinyl acetate is a starting monomer unit and in which most or all (70-100%) of the acetate moieties are subsequently hydrolyzed to alcohol moieties. Other vinyl polymers useful in the present invention include, but are not limited to, polyvinyl acetate and polyvinyl pyrrolidone. Copolymers such as PVA-methylmethacrylate copolymer may also be used in the present invention. PVA is commercially available in a wide range of molecular weights, viscosities and varying degrees of hydrolysis from the polyvinyl acetate precursor.

Other polymers useful for this invention include polymers that form hydrogels such as Carbopol®, acidic carboxy polymers; Cyanamey-O polyacrylamides; cross-linked indene-maleic anhydride polymers, Polyox® polyethylene oxide polymers; starch graft copolymers; Aqua-Keepso acrylate polymer polysaccharides composed of condensed glucose units such as diester cross-linked polyglucan, and the like. Representative polymers that form hydrogel are shown in U.S. Pat. Nos. 3,865,108; 4,002,173; 4,207,893; and in Handbook of Common Polymers, by Scott and Roff, published by the Chemical Rubber Company, Cleveland, Ohio.

A solid material, which contains immobilized retinal analog-containing proteorhodopsin in a hydrophilic polymer or in a mixture of hydrophilic polymers, can be prepared by the steps of first mixing a hydrophilic polymer or its precursor with proteorhodopsin in water or an aqueous buffer to form a homogeneous solution, then solidifying the polymer, wherein the proteorhodopsin molecules are immobilized in the polymer. The solidification of the polymer is carried out by drying, cooling, curing, or polymerization.

For example, a polyvinyl alcohol material containing immobilized retinal analog-containing proteorhodopsin can be prepared by the method comprising the steps of: (a) mixing polyvinyl alcohol, water or a buffer having pH between about 3-12, and analog-containing proteorhodopsin to form a solution; (b) spreading the solution on the surface of a solid; and (c) drying the solution to form a polyvinyl alcohol material having immobilized analog-containing proteorhodopsin.

A polyacrylamide material that contains immobilized retinal analog-containing proteorhodopsin can be prepared by the method comprising the steps of (a) mixing acrylamide, bisacrylamide, membrane-free analog-containing proteorhodopsin, and one or more polymerization initiators in water or a buffer having pH between 3-12; and (b) polymerizing acrylamide gel; whereby the proteorhodopsin is immobilized within the polyacrylamide gel matrix. The polymerization initiators commonly used include ammonium persulfate and N,N,N',N'-tetramethylethylenediamine (TEMED). Alternatively, the method comprises the steps of (a) mixing acrylamide, bisacrylamide, membrane-free analog-containing proteorhodopsin, and one or more UV-activated free radical generators in water or a buffer having pH between 3-12; and (b) exposing the mixture to UV light to polymerize acrylamide gel. The UV-activated free radical generators include riboflavin and TEMED (used together), 2,2-Dimethoxy-2-phenyl acetophenone (DMPA), and those described in the SE96047-3 patent.

Sol-gels that contain immobilized retinal analog-containing proteorhodopsin can be prepared by the method comprising the steps of: (a) adding to a silane precursor an acidic solution having pH 1.5-4 to hydrolyze the silane precursor to form silicate sol; (b) adding to the silicate sol an aqueous solution having analog-containing proteorhodopsin at pH about 5-9; and (c) incubating (b) to form a gel; whereby the proteorhodopsin is immobilized within the sol gel matrix. The silane precursors include tetraalkylorthosilicate, alkyltrialkoxysilane, aryltrialkoxysilane, dialkyldialkoxysilane, diaryldialkoxysilane, alkali metal silicate, polyol silicate, polyol siloxane, poly(methyl silicate), and alcohol-free poly(silicic acid). Preferred silane precursors are tetraalkylorthosilicate and poly(glyceryl)silicate.

Gelatin that contains immobilized retinal analog-containing proteorhodopsin can be prepared by the method comprising the steps of: (a) heating and dissolving gelatin in water or a buffer to form a homogeneous aqueous gelatin solution; (b) cooling the gelatin solution to about 39-45° C.; (c) mixing the cooled gelatin solution with retinal analog-containing proteorhodopsin; and (d) incubating (c) to form a gel; whereby the retinal analog-containing proteorhodopsin is immobilized within the gelatin gel matrix.

Technical Application of Retinal Analog-Containing Proteorhodopsins

The retinal analog-containing proteorhodopsins have many technical applications. For example, they can be incorporated into instruments or devices having photochromic applications, photoelectric applications, and/or phototransport applications.

Under photochromic applications, the retinal analog-containing proteorhodopsins can be used for its light absorption properties for optical data storage, interferometry and/or photonics. Photochromic applications include, but are not limited to, holographic film. The retinal analog-containing proteorhodopsins can be used for optical data storage devices, such as 2-D storage, 3-D storage, holographic storage, associative storage, or the like. The retinal analog-containing proteorhodopsins can be used in a device for information processing, such as optical bistability/light switching, optical filtering, signal conditioning, neural networks, spatial light modulators, phaseconjugation, pattern recognition, interferometry, or the like.

Under phototransport applications, the retinal analog-containing proteorhodopsins can be used for its light-induced proton transport across a membrane, such as photovoltaic device. One such photovoltaic device is a light-driven energy generator comprising the proteorhodopsin, whereby light energy can be converted to chemical energy. The retinal analog-containing proteorhodopsins can also be used in devices for ATP generation in reactors, desalination of seawater, and/or conversion of sunlight into electricity.

The retinal analog-containing proteorhodopsins can also be used in devices for 2D harmonic generation, radiation detection, biosensor applications, or the like.

In one embodiment, the invention provides a material suitable for an optical information carrier. Particularly, the material is suitable for optical data storage material or fraud-proof optical data carrier.

In one embodiment, the invention provides material suitable for the processing and storage of optical information.

In one embodiment, the invention provides a material for use in storing (writing) optical data, the material being capable of retaining data while permitting nondestructive detection (reading) of such data, and being capable of reuse after optical erasure of data.

In one embodiment, the invention provides an information carrier material that is difficult for counterfeiters to mimic.

In one embodiment, the invention provides fraud-proof ink that changes color upon exposing to light.

The present invention provides an optical information carrier comprising a solid material having immobilized retinal analog-containing proteorhodopsin and a substrate such as glass, paper, metal, fabric material, plastic material, wherein said solid material is deposited on said substrate. For example, the substrate is a disk, a card, or a document. The optical information carrier of the present invention may be in the form of a thin film or membrane, which may be referred to as a two-dimensional film, or may be in the form of a thick film which may be referred to as a three-dimensional layer or block. The solid material can range in thickness from a thinly deposited layer orders of magnitude larger in two dimensions than in the third dimension to a thickly cast object with all dimensions of comparable magnitude. The optical information carrier so produced includes proteorhodopsin molecules that can then be exposed to light to convert the molecules from the basal state to the M state.

The basal absorption maxima of all-trans-retinal-containing proteorhodopsins are in general between 480 nm and 530 nm, often between 488 and 526 mm. The basal absorption maxima of retinal analog-containing proteorhodopsins of the present invention in general range from 550-750 nm, preferably 600-700 nm, more preferably 625-650 nm.

The absorption maxima of the M-state of proteorhodopsins in general are between 350 nm and 450 nm, often about 410 nm. The M-state is distinguished from other identified spectral states, the K-, N- and O-like states, which all have red-shifted absorption spectra (e.g. >530 nm) compared with the basal state.

One advantage of using proteorhodopsin as an optical information carrier is that proteorhodopsin can be functionally expressed in E. coli to produce a large quantity (grams or kilograms) of protein economically and efficiently. The proteorhodopsin-expressing cells are lysed and the pellets containing the membrane fraction are collected. The proteorhodopsin protein can be further extracted from the membrane by detergent solubilization. Either the membrane or fragments of membrane that contains proteorhodopsin, or the purified proteorhodopsin protein can be immobilized in a hydrophilic polymer and used as an optical information carrier such as an optical data storage material or a fraud-proof data carrier.

Another advantage of using proteorhodopsin as an optical information carrier is that unlike bacteriorhodopsin, which forms 0.2-1 µm sized protein-lipid patches, membrane-free or detergent-solubilized proteorhodopsin does not cause light scattering. Detergent-solubilized proteorhodopsin is usually in the form of a monomer (about 5 nm in size), and sometimes in the form of an oligomer (dimer, trimer, tetramer, pentamer, or hexamer); such small size does not cause scattering of light in the visible range. Different from bacteriodopsin, proteorhodopsin protein is stable in its monomeric or oligomeric state for at least one month at room temperature, or one year at 4° C. The term "stable" refers to that proteorhodopsin does not change its spectral property significantly (less than 30 nm in maximum absorption wavelength) and is able to produce a photocycle upon excitation by light that includes a transition from the basal state to M-state. The monomeric or oligomeric stability of proteorhodopsin makes it desirable as a component of an optical data storage material without µm-sized particles that scatter light. Additionally, the small size of the individual proteorhodopsin monomers makes it easier to obtain a uniform protein distribution in the optical data storage material.

The advantage of using various retinal analog-containing proteorhodopsins, which have different maximum absorbance wavelengths, in optical data storage, is that it increases capacity of the data storage and allows parallel data processing.

The present invention provides a fraud-proof data carrier comprising a solid material having immobilized one or more analog-containing proteorhodopsins. The material containing immobilized proteorhodopsin can be spread, sprayed, solidified, printed, deposited or dried on the surface of glass, paper, fabric materials, plastic material, metal surface or mineral surface for use as a fraud-proof data carrier. The material containing immobilized proteorhodopsin can also be shaped in a mold to form the three-dimensional fraud-proof data carrier.

For example, the solid material is deposited on products such as banknotes, documents, ID cards, passports, drivers' licenses, keycards, checks, securities, stickers, foils, containers, product packing materials, and the like, to guarantee the authenticity of the products. When proteorhodopsin is exposed to light of excitation wavelength, it is excited to an activated M-state and changes to a yellow color. The color is reverted to its basal color either spontaneously with time or by exposing the material to a second light. For example, the proteorhodopsin-containing material is excited by a yellow light or a green light to change color from red or purple to yellow; the color change is erased spontaneously or by illuminating the material with purple or blue light. The color change is reversible between the basal state and M-state, which provides protection against falsification. The write-read-erase cycle can be repeated multiple times without any observable change in the property of the material. Conventional inks based on pigments or organic dyes cannot mimic this color change. The color change feature makes the proteorhodopsin material difficult for counterfeiters to mimic. By using retinal analog-containing proteorhodopsins, different basal colors can be provided in security ink or documents, which makes it even more difficult to counterfeit.

As an added security, solid materials containing different colored proteorhodopsins can be deposited at different localized surface regions on banknotes, ID cards, passports, drivers' licenses, keycards, checks, securities, stickers, foils, containers, etc. These different colored proteorhodopsins can be any combination of all-trans-retinal-containing proteorhodopsins and retinal analog-containing proteorhodopsins, as long as they have different maximum absorbance wavelengths.

With different retinal analog-containing proteorhodopsins, it is possible to make multi-color security features on different localized regions of a single fraud-proof document, instead of a single color. The multi-color security features make the forgery even more difficult.

Alternatively, a solid material can be prepared to contain several different colored proteorhodopsins. Such solid material can be prepared by using a mixture containing several different colored proteorhodopsins following the same steps as described above for preparing a solid material containing immobilized retinal analog-containing proteorhodopsin. Such solid material can be deposited at surface regions on banknotes, ID cards, passports, drivers' licenses, keycards, checks, securities, stickers, foils, containers, etc. For example, by selecting proper analog-containing proteorhodopsins and retinal-containing proteorhodopsins, some proteorhodopsins will be excited from B-state to M-state by a green laser, and some proteorhodopsins will be excited by a red laser.

The present invention further provides a security ink comprising one or more hydrophilic polymers and a photochromic material having a proteorhodopsin apoprotein and a retinal analog, wherein the photochromic material and the hydrophilic polymers form a homogeneous liquid phase, said ink solidifies or dries after application onto a surface, thereby immobilizing proteorhodopsin onto a specific location where the ink is applied.

The following examples further illustrate the present invention. These examples are intended merely to be illustrative of the present invention and are not to be construed as being limiting.

EXAMPLES

Example 1

Preparation of Retinal Analog-Containing Proteorhodopsins (Natural Form)

The proteorhodopsin expression plasmids (pTrcHis2-Bac31A8, and pTrcHis2-Hot75 ml) and the control plasmid pTrcHis2-LacZ (Invitrogen) were transformed into competent cells of the strain E. Coli BL21-Codonplus-RIL (Stratagene) as described by the manufacturer. The transformed cells were plated on LA (Luria Agar)+0.5% glucose+100 µg/ml carbenicillin+25 µg/ml chloramphenicol plates and incubated overnight at 37° C. Cells from these plates were grown in 6 ml medium containing LB (Luria Broth)+0.5% glucose+100 µg/ml carbenicillin+25 µg/ml chloramphenicol+10 µM all-trans-retinal or one of the retinal analogs (Compound A, B, C, and DMCA) in glass tubes at 37° C. for 6 hours, where the cells reached early stationary phase. The cells constitutively express proteorhodopsins from the uninduced pTrc promoter. The cells were collected by centrifugation at 4,500×g for 6 minutes, the medium was discarded and the cells were resuspended in 5 ml sterile water. A 900 µl sample of cells was added to a 100 µl aliquot of 1.0 M CHES (pH 9.5).

Example 2

Spectra of Retinal Analog-Containing Proteorhodopsins (Natural Form) in Intact Cells The spectra of the all-trans-retinal-containing proteorhodopsin and retinal analog containing proteorhodopsin were measured in intact cells using a spectrophotometer (On-Line Instrument Systems, Inc.) adapted for use with turbid samples by placing the photomultiplier detector adjacent to the sample cuvette. The absorption from a strain containing a control plasmid (pTrcHis2-LacZ) was subtracted from proteorhodopsin containing samples. To correct for differences in background light scattering caused by variations in cell densities between the sample and the reference, a linear baseline determined by least-squares fitting of the first ten and last ten wavelength and absorbance values in each spectrum was subtracted from each spectrum. The spectra were then adjusted to the same minimum value by subtracting the differences in minimum values.

Typical proteorhodopsin spectra, such as Bac31A8 and Hot75 ml, inside intact cells at different pH values, were constructed by plotting absorbance vs. wavelength.

Table 1 shows the maximum absorbance wavelength of the all-trans-retinal or analog-containing proteorhodopsins at pH 9.7. The analog-containing proteorhodopsins produced a red-shift of the maximum absorbance compared with the retinal-containing proteorhodopsin.

TABLE 1

| Maximum Absorbance Wavelength (nm) | | |
|---|---|---|
| Compound | Bac 31A8 | Hot75m1 |
| All-Trans-Retinal | 520 | 490 |
| Analog A | 612 | |
| Analog B | 620 | 583 |
| Analog C | 648 | 610 |
| DMAC | | 583 |

Example 3

Purification of Retinal Analog-Containing Proteorhodopsins (Natural Form)

The results described in Example 2 were obtained with proteorhodopsins in intact cells, where the protein was present in the cytoplasmic membrane. To characterize the spectral properties of proteorhodopsin containing analogs in the absence of other cell components, the all-trans-retinal and retinal analog containing Bac31A8 and Hot75 ml proteorhodopsins were purified as described below.

The proteorhodopsin expression plasmids (pTrcHis2-Bac31A8, and pTrcHis2-Hot75 ml) were transformed into competent cells of the strain BL21-Codonplus-RIL (Stratagene) as described by the manufacturer. The transformed cells were plated on LA+0.5% glucose+100 µg/ml carbenicillin+25 µg/ml chloramphenicol plates and incubated overnight at 37° C. Cells from these plates were grown in 200 ml medium containing LB+0.5% glucose+100 µg/ml carbenicillin+10 µM all-trans-retinal or retinal analog (Compound A, B, C, or DMCA) at 37° C. in baffled 500 ml shakeflasks. The cultures were inoculated directly from fresh transformation plates. Proteorhodopsin expression in the different cultures were induced when the $OD_{600}$ of the cultures were approximately 0.8 (after 4 hours growth) by adding 0.5 mM IPTG+10 µM all-trans-retinal or retinal analog and the cultures were incubated for additional 4 hours at 37° C. The cells were harvested by centrifugation at 3,500×g for 10 minutes and stored at −80° C. Cells were resuspended in lysis buffer containing 50 mM Tris pH 7.7 and protease inhibitors (Complete, EDTA-free Protease Inhibitor Cocktail Tablets from Roche Applied Science); and lysed at 0° C. by three passages through a French pressure cell. Intact cells and other insoluble debris were removed by centrifugation at 15,000×g for 30 minutes. Cell membranes were collected by centrifugation at 500,000×g for one hour. The membranes were suspended in 50 mM Tris pH 7.7, protease inhibitors (Complete, EDTA-free Protease Inhibitor Cocktail Tablets from Roche Applied Science), and 2% dodecyl-β-D-maltoside using a tissue homogenizer. The solubilized membrane fraction was incubated 16 hours with the resin in Talon spin columns (Clontech) that had been equilibrated with 1 ml wash buffer containing 50 mM Tris, pH 7.7 and 0.5% dodecyl-β-D-maltoside. The resin was washed three times with 1 ml wash buffer containing 50 mM Tris, pH 7.7 and 0.5% dodecyl-β-D-maltoside. Proteorhodopsins were eluted from the resin two times with 0.5 ml elution buffer containing 50 mM Tris pH 7.7, 0.5% dodecyl-β-D-maltoside and 250 mM EDTA. The two elutates were pooled and EDTA was removed by three successive ten-fold concentrations using a Microcon YM-10 centrifugal filter unit (Millipore) and dilutions with a buffer containing 50 mM Tris, pH 7.7 as described by the manufacturer. The proteorhodopsin samples were then concentrated ten-fold and stored at 4° C.

Example 4

Spectra of Purified Retinal Analog-Containing Proteorhodopsin (Natural Forms)

5 µl purified proteorhodopsin was diluted in 500 µl of buffer containing 100 mM either citrate (pH 5.09), or CHES (pH 9.50). Wavelength spectra from 250 nm to 800 nm were obtained at room temperature on a Cary3 spectrophotometer (Varian).

Figure 1:
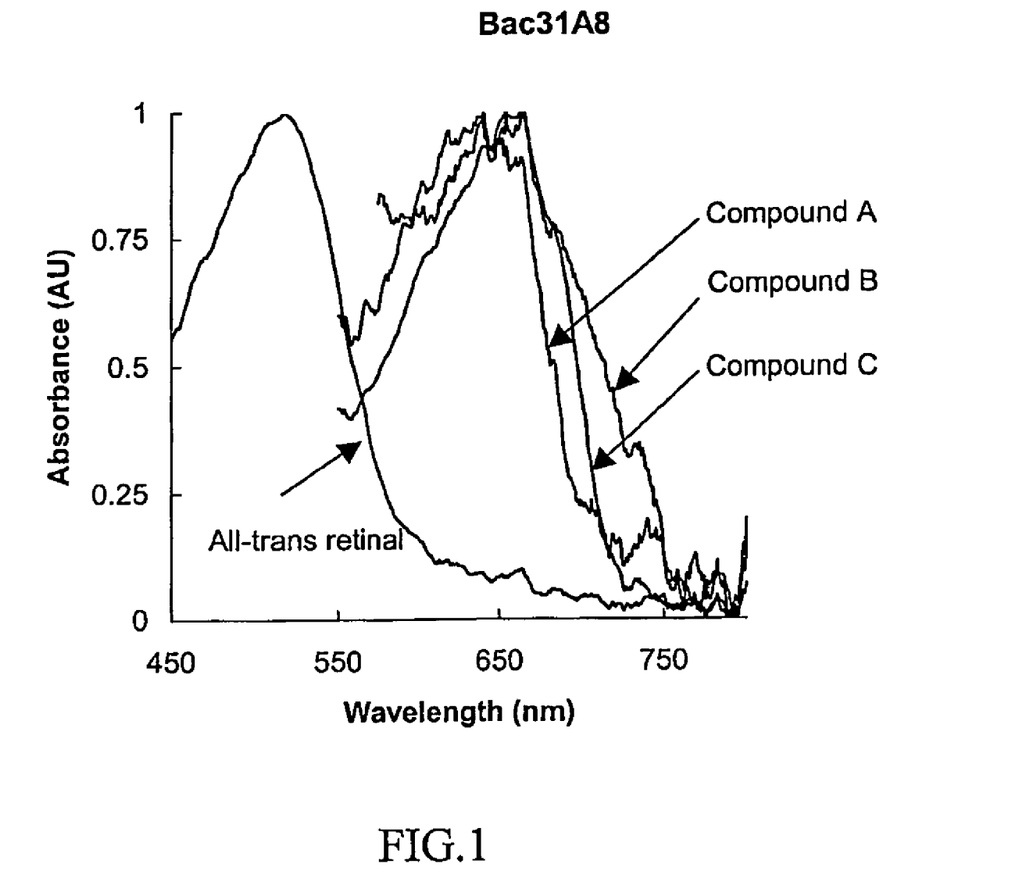
FIG. 1 shows the spectra of detergent-solubilized and purified Bac31A8 proteorhodopsin that contains all-trans-retinal or retinal analogs (Compound A, B, or C) at pH 9.7.

FIG. 1 shows the spectra of detergent-solubilized and purified Bac31A8 proteorhodopsin that contains all-trans-retinal or retinal analogs (Compound A, B, or C) at pH 9.7.

Figure 2:
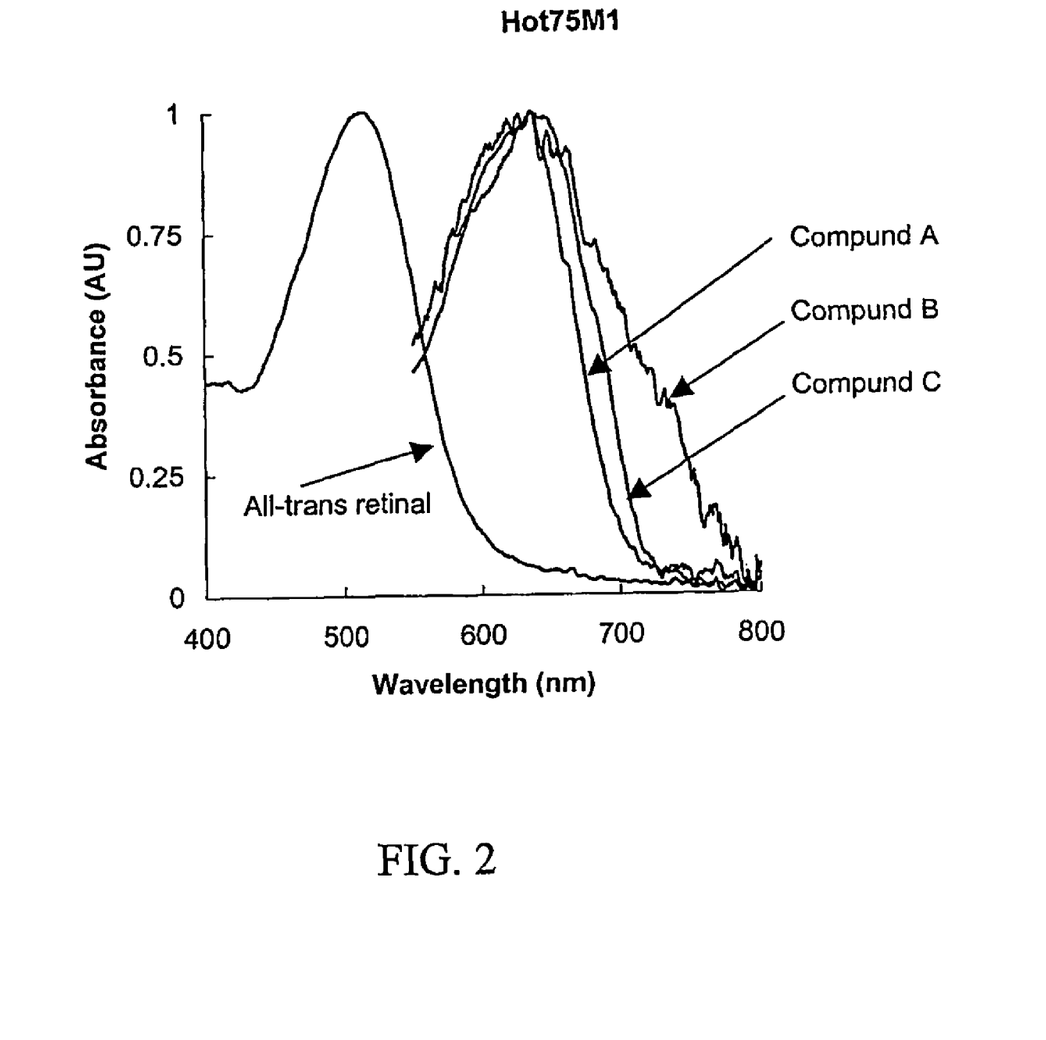
FIG. 2 shows the spectra of detergent-solubilized and purified Hot75M1 proteorhodopsin that contains all-trans-retinal or retinal analogs (Compound A, B, or C) at pH 9.7.

FIG. 2 shows the spectra of detergent-solubilized and purified Hot75M1 proteorhodopsin that contains all-trans-retinal or retinal analogs (Compound A, B, or C) at pH 9.7.

The results show that that analog (Compound A, B, or C)-containing proteorhodopsins exhibit different spectra when compared with the all-trans-retinal-containing proteorhodopsin. A large red shift of the absorbance spectra (>120 nm) is observed with the retinal analog-containing proteorhodopsins.

Example 5

Incorporation of Retinal Analog into Proteorhodopsin Mutant

Compound B was incorporated into proteorhodopsin mutant Bac31A8E108Q by the protocols similar to those described in Examples 1 and 3, except (a) expression plasmid (pTrcHis2-Bac31A8-E108Q) was used and (b) Compound B was added to proteorhodopsin after French press, homogenization, column extraction, and centrifugation concentration procedures.

The incorporated Compound B has two peaks of maximum wavelength at 640 and 480 nm.

Example 6

Photocycles of Retinal Analog-Containing Proteorhodopsin Mutant

Compound B-containing Bac31A8E108Q proteorhodopsin sample in 250 mM CAPS buffer pH 11 was placed in a cuvette. The absorbance at 640 nm was measured by a spectrophotometer continuously while the sample was irradiated with a light source coupled with 630, 610, or 475 nm cut-off filters between 20-60 seconds. The light source was turned on at t=20 second, and turned off at t=60 second.

Figure 3:
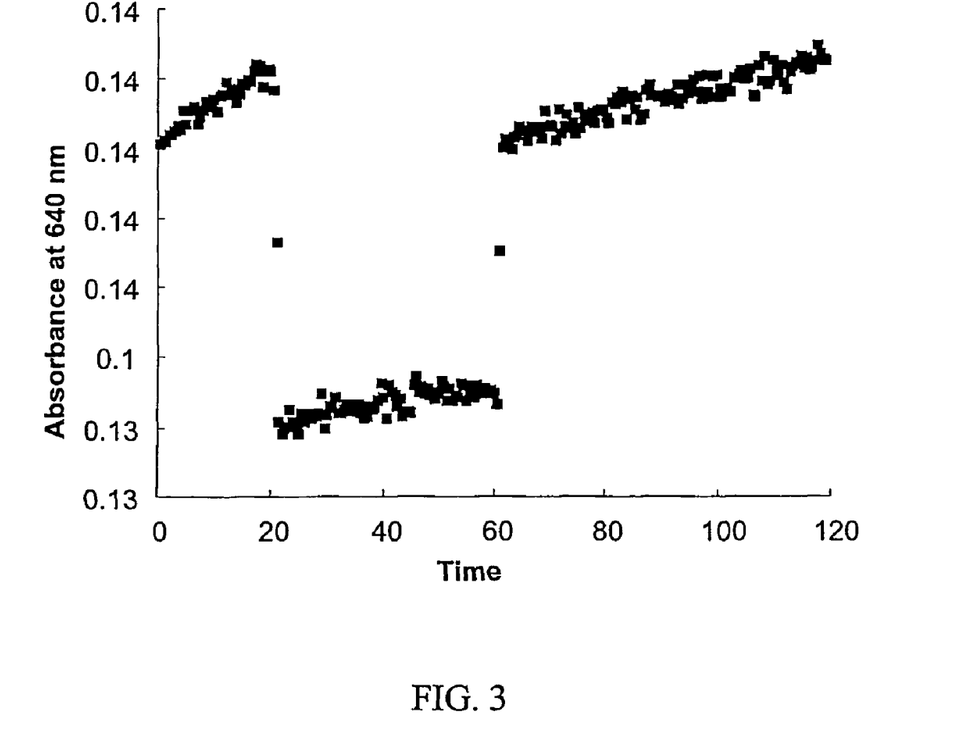
FIG. 3 shows the absorbance at 640 nm of Compound B-containing Bac31A8E108Q proteorhodopsin vs. time. The proteorhodopsin was irradiated with light coupled with a 630 nm light filter. The light was turned on at t=20 second and turned off at t=60 second.

FIG. 3 shows the graph of the time trace of absorbance at 640 nm with a 630 nm light filter. When the light shone on the sample between 20-60 seconds, the absorbance decreased sharply and stayed about the same throughout the time that the light was on. After the light was turned off at 60 second, the absorbance reversed back immediately. The 610 nm light filter produced similar time trace graph.

Figure 4:
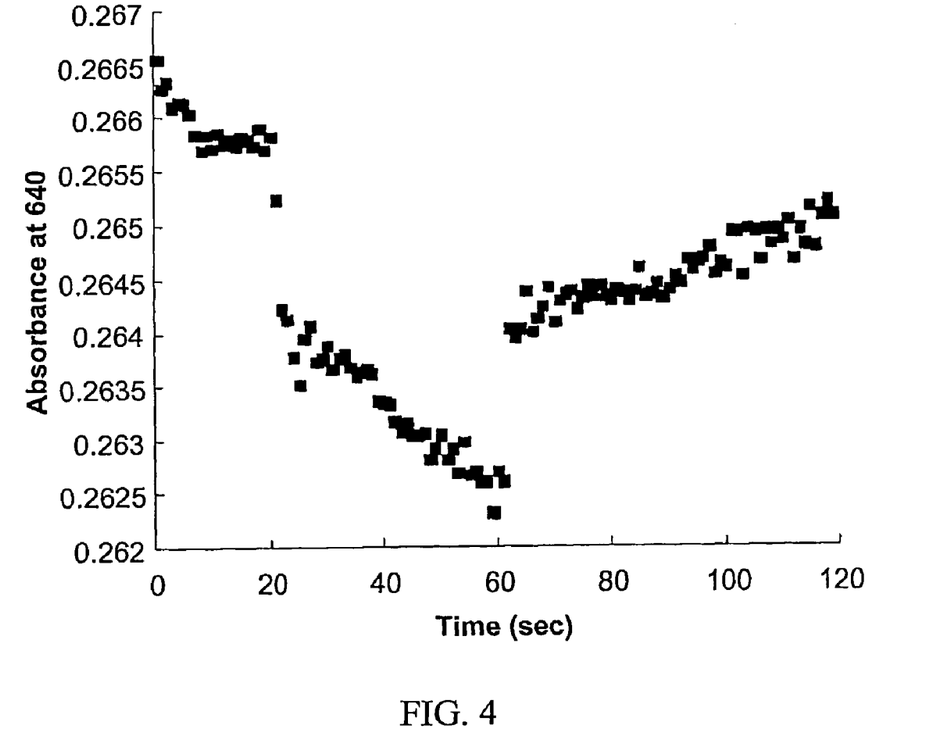
FIG. 4 shows the absorbance at 640 nm of Compound B-containing Bac31A8E108Q proteorhodopsin vs. time. The proteorhodopsin was irradiated with light coupled with a 475 nm light filter. The light was turned on at t=20 second and turned off at t=60 second.

FIG. 4 shows the graph of the time trace of absorbance at 640 nm with a 475 nm light filter. When the light shone on the sample between 20-60 seconds, the absorbance decreased sharply and had a continuous downward slope throughout the time that the light was on. After the light was turned off at 60 second, the absorbance increased suddenly.

FIGS. 3 and 4 demonstrate that the 640 nm absorbance of Compound B-containing Bac31A8E108Q proteorhodopsin decreases and increases in response to on/off of light, which are characteristics of photocycles.

Although the invention has been described with reference to the presently preferred embodiments, it should be understood that various modifications could be made without departing from the scope of the invention.

What is claimed is:

1. A photochromic material comprising a proteorhodopsin apoprotein and an azulenic retinoid compound of Formula I, Formula I wherein R', R" and R'" are each independently H, $C_{1-4}$ straight chain alkyl, or $C_{1-4}$ branched chain alkyl, n is an integer from 1 to 4;

$X_a$ and $X'_b$ are each independently H, $C_{1-4}$ alkyl, F, Cl or $CF_3$;

Y is absent, or Y is a para-, meta-, or ortho- phenyl; and

Z is CHO.

2. The photochromic material according to claim 1, wherein said R', and R'" are a $C_{1-4}$ straight chain alkyl, and R" is a $C_{1-4}$ branched chain alkyl.

3. The photochromic material according to claim 2, wherein R'=R'"=methyl, and R"=isopropyl.

4. The photochromic material according to claim 1, wherein Y is absent.

5. The photochromic material according to claim 1, wherein said azulenic retinoid compound is selected from the group consisting of Compound A, B, C, D, E, F, G, H, I, J, K, L, M, and N:

Compound A

Compound B

Compound C

Compound D

Compound E

-continued

Compound F

Compound G

Compound H

Compound I

Compound J

Compound K

Compound L

-continued

Compound M

Compound N

6. A photochromic material comprising a proteorhodopsin apoprotein and a retinal analog, wherein said retinal analog is selected from the group consisting of p-dimethyl aminocinnamaldehyde, Compound O, P, Q, R and S:

P-dimethyl aminocinnamaldehyde

Compound O

Compound P

Compound Q

Compound R

-continued

Compound S

7. The photochromic material according to claim 1 or 6, wherein said photochromic material has spectral properties different from the spectral properties of a corresponding photochromic material comprising said proteorhodopsin apoprotein and all-trans-retinal.

8. The photochromic material according to claim 7, wherein said photochromic material has an absorption spectrum that does not overlap significantly with the absorption spectrum of the corresponding photochromic material.

9. The photochromic material according to claim 7, wherein said photochromic material has a maximum absorbance wavelength that is red-shifted compared with the maximum absorbance wavelength of the corresponding photochromic material.

10. The photochromic material according to claim 9, wherein the maximum absorbance wavelength of said photochromic material is between 550 and 750 nm.

11. The photochromic material according to claim 10, the maximum absorbance wavelength of said photochromic material is between 600 and 700 nm.

12. The photochromic material according to claim 1 or 6, wherein said proteorhodopsin apoprotein is derived from BacA8 or a mutant thereof.

13. The photochromic material according to claim 1 or 6, wherein said proteorhodopsin apoprotein is derived from Hot75 ml or a mutant thereof.

14. A solid material comprising the photochromic material according to claim 1 or 6.

15. The solid material according to claim 14, wherein said solid material further comprises one or more hydrophilic polymers that are capable of forming a homogeneous phase with said photochromic materials prior to solidification to a solid form.

* * * * *